United States Patent [19]
Brunner et al.

[11] Patent Number: 5,777,141
[45] Date of Patent: Jul. 7, 1998

[54] PROCESS FOR RECOVERING UNSATURATED FATTY ACIDS AND DERIVATIVES THEREOF

[75] Inventors: Gerd Brunner, Hamburg; Frank Reichmann, Burgdorf, both of Germany

[73] Assignee: Roche Vitamins Inc., Parsippany, N.J.

[21] Appl. No.: 699,883

[22] Filed: Aug. 16, 1996

[30] Foreign Application Priority Data

Aug. 17, 1995 [CH] Switzerland .............................. 2355/95

[51] Int. Cl.$^6$ .............................. C07C 51/47; C07C 67/56
[52] U.S. Cl. .............................. 554/175; 554/194
[58] Field of Search .............................. 554/175, 194

[56] References Cited

U.S. PATENT DOCUMENTS

| | | | |
|---|---|---|---|
| 4,880,543 | 11/1989 | Khosah et al. | 210/635 |
| 5,061,505 | 10/1991 | Cully et al. | 426/601 |
| 5,362,895 | 11/1994 | Engelhardt et al. | 554/175 |

FOREIGN PATENT DOCUMENTS

| | | |
|---|---|---|
| 0 558 974 | 2/1993 | European Pat. Off. |
| 741 359 | 11/1943 | Germany . |
| 62 292744 | 9/1987 | Japan . |
| 94/25552 | 11/1994 | WIPO . |

OTHER PUBLICATIONS

Abstract corresponding to JP 62 292744, 1987.

Kontakte (Darmstadt) 1992 (1), pp. 12–15: "Alkalines–stable Stationary Phases for HPLC (Part 1): Aluspher®A1".

M. Perrut, LC–GC (Magazine of Liquid and Gas Chromatography), vol. 6(10), p. 914 (1988).

*Primary Examiner*—Richard L. Raymond
*Attorney, Agent, or Firm*—George W. Johnston; William H. Epstein; John P. Parise

[57] ABSTRACT

A process for the recovery of unsaturated fatty acids with at least 16 carbon atoms in the molecule or a derivative of such a fatty acid from a mixture of fatty acids and/or fatty acid derivatives by column chromatography with supercritical or liquid carbon dioxide as the mobile phase comprises using aluminum oxide, optionally pretreated with alkali, as the stationary phase. The pre-treatment of the aluminum oxide is conveniently effected by contacting the particulate aluminum oxide with an aqueous solution of an alkali metal or alkaline earth metal hydroxide, optionally supplemented with a water-miscible or water-soluble organic solvent, in the pH range of about 10 to about 13 over several hours. The unsaturated fatty acids or fatty acid derivatives produced chromatographically in this manner are suitable as valuable active agents in the fields of nutrition and medicine.

14 Claims, 5 Drawing Sheets

PROCESS FOR RECOVERING UNSATURATED FATTY ACIDS AND DERIVATIVES THEREOF

BACKGROUND OF THE INVENTION

1. Field

The present invention is concerned with a column chromatography process for the recovery of unsaturated, optionally derivatized fatty acids. A desired fatty acid can be recovered from mixtures containing other unsaturated, optionally derivatized fatty acids, or from mixtures containing other components, such as saturated, optionally derivatized fatty acids.

2. Description

Scientific interest from a nutritional and medical point of view in unsaturated, especially polyunsaturated, fatty acids "PUFAs" has prevailed for a long time. As is known, certain fatty acids (especially PUFAs) are precursors of prostanoid compounds, such as prostaglandins, thromboxanes, and leukotrienes. These prostanoid compounds play an important biological role in, among other things, thrombocyte aggregation, inflammation, and allergies.

In particular, the two "ω-3"-PUFAs—eicosapentaenoic acid ("EPA") and docosahexaenoic acid ("DHA")—are useful as active agents in the treatment and prevention of "civilization disorders", especially cardiovascular disorders such as cardiac infarct and elevated cholesterol levels. In ω-3-PUFAs the first double bond is situated at the third carbon atom from the terminal methyl group of the acid, and in ω-6-PUFAs the first double bond is situated at the sixth carbon atom from the terminal methyl group.

The ω-3-PUFAs and ω-6-PUFAs play an essential role in general infant development, and in particular, retina, and brain development. Breast-fed children develop significantly more rapidly than comparable children who are not suckled (ω-3- and ω-6-PUFAs can be detected in mother's milk). EPA and DHA are currently under intensive investigation with respect to their positive activities in controlling arteriosclerosis, lowering of cholesterol and blood fat levels, and preventing thrombocyte aggregations and chronic inflammations, such as rheumatoid arthritis, neurodermatitis, and allergies.

Natural fats and oils, especially fish, sea animal and vegetable oils, are important sources of ω-3-and ω-6-PUFAs. These PUFAs are primarily present in the form of their glycerides and phospholipids, and are accompanied by many undesired secondary products and impurities. EPA and DHA occur mainly in fish oils. In contrast, the ω-6-PUFAs, arachidonic acid and linoleic acid, are primarily present in animal fats and vegetable oils, such as corn oil.

Unfortunately, the total content of desired long-chain PUFAs in alimentary fats and oils lies in the range of about 10 to 21% (for example, ω-3- and ω-6-PUFAs in fish oils in the range of about 12 to 18%). Accordingly, large amounts of fish must be consumed in the diet daily to achieve the recommended dosage of ω-3-PUFAs. Of course, such fish consumption would be impracticable. Therefore, some producers, in addition to the established practice of marketing fish oils containing the oils in natural concentration, are now marketing capsules containing enriched PUFAs in the purest possible form (as esters or as re-substituted triglycerides). A demand currently exists for purified individual PUFAs.

Alkaline hydrolysis of the mixtures containing the PUFAs (for example the fish, sea animal or vegetable oils themselves or refined forms thereof) and subsequent re-esterification with alcohols (especially with ethanol) yields, among other things, the corresponding alkyl esters. As is known, subsequent separation of an alkyl ester mixture can be effected by countercurrent extraction with a supercritical gas, especially carbon dioxide. Substantial separation can be achieved based on the number of carbon atoms present in the alkyl ester. Relatively pure fractions of PUFAs having the same or a relatively close carbon atom number can be obtained in this manner, for example, a 60% pure mixture of EPA ($C_{20}$) and DHA ($C_{22}$). From experience, a planned separation in this manner based on the degree of saturation (number of double bonds) is not possible.

To investigate physiological activities of individual PUFAs, fractions of significantly higher purity are required. Because of previously inadequate separation methods, it has been impossible to clarify whether EPA and DHA act separately or in conjunction with one another. The same problem existed for docosapentaenoic acid which is always by necessity administered with DHA.

Accordingly, there has been a long felt need for a process for separating PUFAs (especially the nutritionally and medicinally interesting PUFAs having at least 16 carbon atoms) and thus to make available individual PUFAs, not only according to the number of carbon atoms, but also according to the number of double bonds. Such individual PUFAs would not only represent a supplement to daily nutrition, but could also be administered specifically as medicaments.

Certain publications, most of which being based on the work of groups led by M. Perrut [see, for example, LC-GC (Magazine of Liquid and Gas Chromatography) 6, 10 (1988), 914], are available in the field of preparative supercritical fluid chromatography ("SFC"). According to these publications, docosapentaenoic acid and DHA, obtained from fish oil and re-esterified to the corresponding ethyl esters, can be separated preparatively on packed columns using SFC. EPA and DHA of 96% and 85% purity, respectively, could be achieved using a silica-packed column. Information relating to the separation of docosapentaenoic acid is not given. However, the relatively low docosahexaenoic acid purity (85%) suggests that it was not possible to separate docosapentaenoic acid in this manner.

A SFC column chromatographical process for the recovery of unsaturated fatty acids or derivatives thereof from vegetable or animal mixtures containing these has become known from European Patent Publication (EP) 558,974. In this process supercritical or liquid carbon dioxide is used as the mobile phase and a specifically defined coated phase is used as the stationary phase. The stationary phase features a basic structure usually consisting of silica gel or aluminum oxide which must be provided with a coating phase having free electron pairs and/or multiple bonds, as are present, for example, in a substance containing an amino group (for example, in aminopropyl) or a nitro group or, respectively, a phenyl group or a cyano group (for example, in cyanopropyl). Effective separation of individual PUFAs by SFC column chromatography with carbon dioxide as the mobile phase, using an uncoated basic structure, especially aluminum oxide, is not suggested in any way in EP 558,974.

SUMMARY OF THE INVENTION

The subject invention provides a process for recovering one or more unsaturated fatty acid entities having at least 16 carbon atoms from a mixture containing fatty acid entities. The term "fatty acid entities" is to include fatty acids, as well as derivatives of fatty acids. The subject process comprises passing the mixture containing the fatty acid entities through a column using an aluminum oxide stationary phase and a liquid-containing $CO_2$ mobile phase. The term "liquid-containing $CO_2$" is to encompass liquid carbon dioxide and supercritical carbon dioxide.

DETAILED DESCRIPTION OF THE INVENTION

The present invention will now be described in terms of the preferred embodiments. These embodiments are set forth to aid in understanding the invention, but are not to be construed as limiting.

The present invention provides a novel process for the recovery of valuable unsaturated fatty acids, as such or as derivatives, especially pre-prepared lower alkyl esters of these fatty acids, from a mixture of the fatty acids and/or fatty acid esters by column chromatography. This process, for the most part, does not have the disadvantages of known processes. The subject process recovers unsaturated fatty acids having at least 16 carbon atoms in the molecule or derivatives of such fatty acids from a mixture of fatty acids and/or fatty acid derivatives by column chromatography, with supercritical or liquid carbon dioxide (collectively "liquid-containing $CO_2$") as the mobile phase, and aluminum oxide, optionally pre-treated with alkali, as the stationary phase.

In principle, the process in accordance with the invention is carried out by bringing together the mixture of fatty acids and/or fatty acid derivatives, which may already be under pressure, with the mobile phase of the supercritical or liquid carbon dioxide. The entire mixture is then applied, optionally followed by additional mobile phase, to the chromatography column packed with the aforementioned stationary phase and eluted. The elution is effected under selected temperature and pressure conditions and, due to the strong interactions between the stationary phase and the individual components of the mixture, a temporal separation of these components is achieved. The components dissolved in carbon dioxide "elyates" which are eluted in succession from the column after sequential detection (determination) are collected in receivers determined by the detection means. Carbon dioxide is removed from each collected material by decompression "volatilization" such that finally the obtained, separated components or "fractions" (among other things, the desired unsaturated fatty acids or fatty acid derivatives) are free of carbon dioxide in the individual receivers. If desired, after elution and emergence from the column the eluate can be subjected to one or more further such chromatographic procedures in order to achieve a still greater separation of the components. This also applies to any fraction lacking the required purity.

If, after carrying out the subject process, a derivative originally present in the mixture (for example, a lower alkyl ester or a naturally occurring triglyceride) of an unsaturated fatty acid having at least 16 carbon atoms is obtained from the mixture used, but further isolation of the fatty acid itself is desired, then this can be obtained from the derivative in a conventional manner, such as by saponifying the lower alkyl ester or triglyceride. Also, where an insufficiently enriched unsaturated fatty acid is obtained after such a chemical treatment, the respective product can be subjected to the process in accordance with the invention until the required purity has been achieved in the resulting elution product.

Any mixture containing at least one unsaturated fatty acid having at least 16 carbon atoms in the fatty acid molecule or a derivative thereof is suitable as the mixture of fatty acids and/or fatty acid derivative used in the subject process. Suitable starting materials for use in the subject process include vegetable or animal oils or fats (including those from sea animals). Such oils or fats may contain, among other things, the desired fatty acids in the form of triglycerides, amides, phospholipids, lactones and salts as well as other fatty acids and derivatives, such as triglycerides etc., thereof, sterols (for example cholesterol), vitamins (for example tocopherols), and materials which are normally considered to be impurities (for example polychlorobiphenyl (PCB), polyaromatic hydrocarbons (PAH), pesticides, dioxins, heavy metals, oxidation and decomposition products of saturated fatty acids or their derivatives, residual solvents or reagents from previously used concentration or purification steps, etc.).

Alternatively, the subject process can utilize previously refined and/or chemically treated, especially esterified or re-esterified, crude material (oil or fat). Preferably, when triglycerides are present, the corresponding oil or fat (optionally previously refined) is (1) subjected to an acidic or basic hydrolysis, with the triglycerides contained therein being converted into the corresponding acids, or (2) esterified with a lower alkyl (especially $C_{1-6}$-alkyl) alcohol (especially ethanol), with the triglycerides of the unsaturated and saturated fatty acids being trans-esterified to the corresponding lower alkyl esters. The hydrolysis or esterification can be effected in a conventional manner.

Preferred raw materials (optionally previously refined and/or chemically treated) are fish oils (for example sardine and tuna oil), since these are valuable sources of EPA and DHA which are in most demand, as well as animal fats and vegetable oils (for example corn oil), since these in turn are valuable sources of arachidonic acid and linoleic acid which are also in great demand, with fish oils being especially preferred raw materials.

The mixture of fatty acids and/or fatty acid derivatives is normally applied without dilution together with the supercritical or liquid carbon dioxide (collectively "liquid-containing $CO_2$") to the chromatography column packed with the stationary phase used in accordance with the invention. Alternatively, the mixture could have been previously dissolved in a suitable solvent (for example, a lower alkane, preferably n-hexane). However, the mixture is preferably used in undiluted form.

Supercritical carbon dioxide used in the subject process is, as is known, the form of carbon dioxide which is maintained at a temperature of at least about 31° C. and at a pressure of at least about 73 bar and is neither purely liquid nor purely gaseous, but is a hybrid of the two physical forms. Liquid carbon dioxide usable as an alternative in the subject process has a temperature of less than about 31° C. and a pressure which lies above about 73 bar. The advantage of using carbon dioxide resides in its non-toxicity, non-flammability and ready removal by decompression of the collected eluates without leaving a potentially harmful residue with the separated unsaturated fatty acid or with a derivative thereof. Further, the carbon dioxide is widely obtainable in high purity and cost-effectively and, if desired, can be used with an organic cosolvent ("modifier"), for example, the n-hexane mentioned above, as well as a lower alkanol (for example methanol or ethanol), and a lower aliphatic ketone (for example acetone), as part of the mobile phase. Since the critical temperature of carbon dioxide is not much higher than room temperature and the unsaturated fatty acids or fatty acid derivatives to be recovered in accordance with the invention are temperature-sensitive (thermolabile), carbon dioxide is also excellently suited for these reasons as the mobile phase used in the subject process.

The aluminum oxide which is used as the stationary phase in the process in accordance with the invention—and which is characteristic of the invention—is conveniently present as unsymmetrical or, preferably, bead-like (spherical) particles which are packed as homogeneously as possible, the particle size being about 5 to 25 mm. Such bead-like aluminum oxide is readily obtainable commercially. As examples of commercially obtainable aluminum oxide there can be mentioned Aluspher® Al and Spherisorb alumina; the former has a specific surface area $S_{BET}$ of 170 m²/g, a pore volume $V_p$ of 0.5 ml/g, a pore diameter D of 100 Å and a particle size $dp_{50}$ of 5 mm, while the latter has a $S_{BET}$ of 93 m²/g, a D of 130 Å and a $dp_{50}$ of likewise 5 mm. Crushed materials are available from various producers, e.g. ICN Biomedicals Inc. These aluminum oxides feature a grain size distribution of 3–6 µm, 7-12 µm, 10–18 µm or 18–32 µm. The specific surface area $S_{BET}$ of these materials is 200 m²/g; the pore volumes and pore diameters are comparable with those of spherical materials.

As an alternative to the direct use of the (untreated) aluminum oxide as the stationary phase, the aluminum oxide can be subjected prior to use to an alkaline pre-treatment. This pre-treatment comprises in principle the contact of the particulate aluminum oxide with an aqueous solution of an alkali metal or alkaline earth metal hydroxide (such as sodium, potassium or calcium hydroxide), in the pH range of about 10 to about 13, over several hours, conveniently over about 8 to about 20 hours. The concentration of the aqueous alkali metal or alkaline earth metal hydroxide solution conveniently lies in the range of about 0.01M to about 0.1M. If desired, the aqueous alkali metal or alkaline earth metal hydroxide solution can be supplemented with a water-miscible or water-soluble organic solvent in order to adjust the viscosity of the solution to a value which is practicable in use. This is achieved, for example, with the polar organic solvent acetonitrile or acetone. The 10:90 (v/v) mixture of acetonitrile and 0.1M aqueous sodium hydroxide solution, which has a pH value of about 13, has been found to be especially suitable.

Alkaline pre-treatment of the aluminum oxide is conveniently effected by continuously passing the alkaline solution through the aluminum oxide already packed in the chromatography column over several hours, preferably about 12 to 16 hours. This is followed by rinsing the thus pre-treated aluminum oxide with distilled water until the rinsings which exit from the column are neutral. To remove residual water from the pre-treated aluminum oxide, it is recommended to heat the column to between 50° and 90° C. for about 4–10 hours and subsequently to rinse the pre-treated aluminum oxide with a lower alkane, preferably n-heptane, for several hours, preferably about 8 to 20 hours. Thereafter, the thus pre-treated aluminum oxide can be used as the stationary phase in the process in accordance with the invention. The use of aluminum oxide pre-treated with alkali represents a preferred aspect of the process in accordance with the invention.

To maintain the carbon dioxide used as the mobile phase in the subject process in the supercritical or liquid range, certain temperature and pressure conditions must be observed, not only during the introduction of the carbon dioxide into the chromatography column packed with the stationary phase, but also during the subsequent elution. The process is conveniently carried out in the temperature range of about 30° C. to about 100° C. and at a pressure of about 140 bar to about 320 bar, with the suitable pressure being lower when aluminum oxide pre-treated with alkali is used in place of untreated aluminum oxide under otherwise equivalent process conditions. Preferably, the temperature range is about 45° C. to about 75° C. and the respective pressure range is about 220 bar to about 260 bar. The density of the carbon dioxide can be adjusted via pressure and temperature, and in the last-mentioned temperature and pressure range the optimal carbon dioxide density is about 720 kg/m³ to about 850 kg/m³.

The aluminum oxide stationary phase used in the subject process brings about the chromatographic separation of the various unsaturated fatty acids or fatty acid derivatives and, if present, saturated fatty acids or fatty acid derivatives. Separation is based on (1) chain length (number of C atoms) and (2) the degree of saturation (number of double bonds—the higher this number, the lower the degree of saturation). From a certain number of double bonds the selectivity with respect to the degree of saturation appears to predominate.

If the fatty acids or fatty acid derivatives to be separated have only one double bond, such as in the case of erucic acid (22 C atoms, 1 double bond: "22:1"), then the selectivity with respect to the chain length is clearly subordinate, and the fatty acids or derivatives elute prior to the range of shorter but more highly unsaturated fatty acids or derivatives, such as in the case of the 20:5 fatty acid eicosapentaenoic acid.

In an elution of the 20:5, 22:5 and 22:6 fatty acids (eicosapentaenoic, docosapentaenoic and docosahexaenoic acid, respectively), the longer-chain acid will be retained on the column longer than the shorter-chain acid with the same number of double bonds. Likewise, the acid having a smaller degree of saturation will be retained on the column longer than the acid having a larger degree of saturation. Thus, for this example, the 20:5 fatty acid is eluted first, the 22:5 fatty acid is eluted second, and the 22:6 fatty acid is eluted third. Especially in the latter range (number of C atoms 20–22 and/or number of double bonds 5–6) there are to be found the unsaturated fatty acids of greatest significance in the fields of nutrition and medicine, where there is need to achieve clear chromatographic separations without excessive tailing.

The temperature and pressure conditions under which the subject process is carried out and the choice between untreated aluminum oxide and aluminum oxide pre-treated with alkali as the stationary phase will exert an influence on the separation result. In general, a temperature increase or pressure reduction temporarily separates out the eluates of the different fatty acids, while a pressure increase or temperature reduction brings together the eluates. By varying these parameters, the course of the subject process can be controlled with respect to time. By alkaline pre-treament of the aluminum oxide the active centers (predominantly Lewis acids and bases) on the surface of the aluminum oxide can be blocked, weakening its polarity. The sequence of the eluates is not altered after this treatment, but the tailing of the polar multiply-unsaturated fatty acids is decreased and the elution times are significantly reduced. If, for example, the 22:6 fatty acid finally eluted when carrying out the process in accordance with the invention at 65° C. and 280 bar on untreated aluminum oxide is eluted only after about half an hour with perceptible tailing, then the elution effected under the same temperature and pressure conditions on the alkaline-treated aluminum oxide is effected after almost a third of the time and with strongly reduced tailing. For this reason the use of an aluminum oxide pre-treated with alkali is preferred over the use of an untreated neutral aluminum oxide in the process in accordance with the invention.

Detection of components dissolved in carbon dioxide "eluates" eluted in succession from the chromatography column is effected sequentially preferably via an ultraviolet "UV" detector, followed by a flame ionization detector "FID". The UV detector permits an evaluation of the components according to the number of double bonds and can accordingly contribute to the limited structural evaluation of individual components. By using FID the distribution of the different eluates in the receivers is performed electronically. Such technology is known per se, as is the manner by which the carbon dioxide is removed (by decompression) from the respective collected material.

The process in accordance with the invention is particularly suitable for the recovery of the 20:5 fatty acid eicosapentaenoic acid as well as the 22:6 fatty acid docosahexaenoic acid, in each case either directly or via a derivative thereof, preferably the ethyl ester.

The invention is illustrated on the basis of the following Examples.

EXAMPLE 1

Performance of the Process

An apparatus from Carlo Erba Instruments (see FIG. 1) is used to investigate the chromatographic recovery of the components, especially the unsaturated fatty acid ethyl esters, from a fish oil esterified with ethanol. The apparatus is supplied continuously with mobile phase via a carbon dioxide ($CO_2$) cylinder. The mobile phase can be operated according to selected pressure and temperature conditions in the supercritical range (with $CO_2$ over about 31° C. and 73 bar) or subcritical range.

Figure 1:
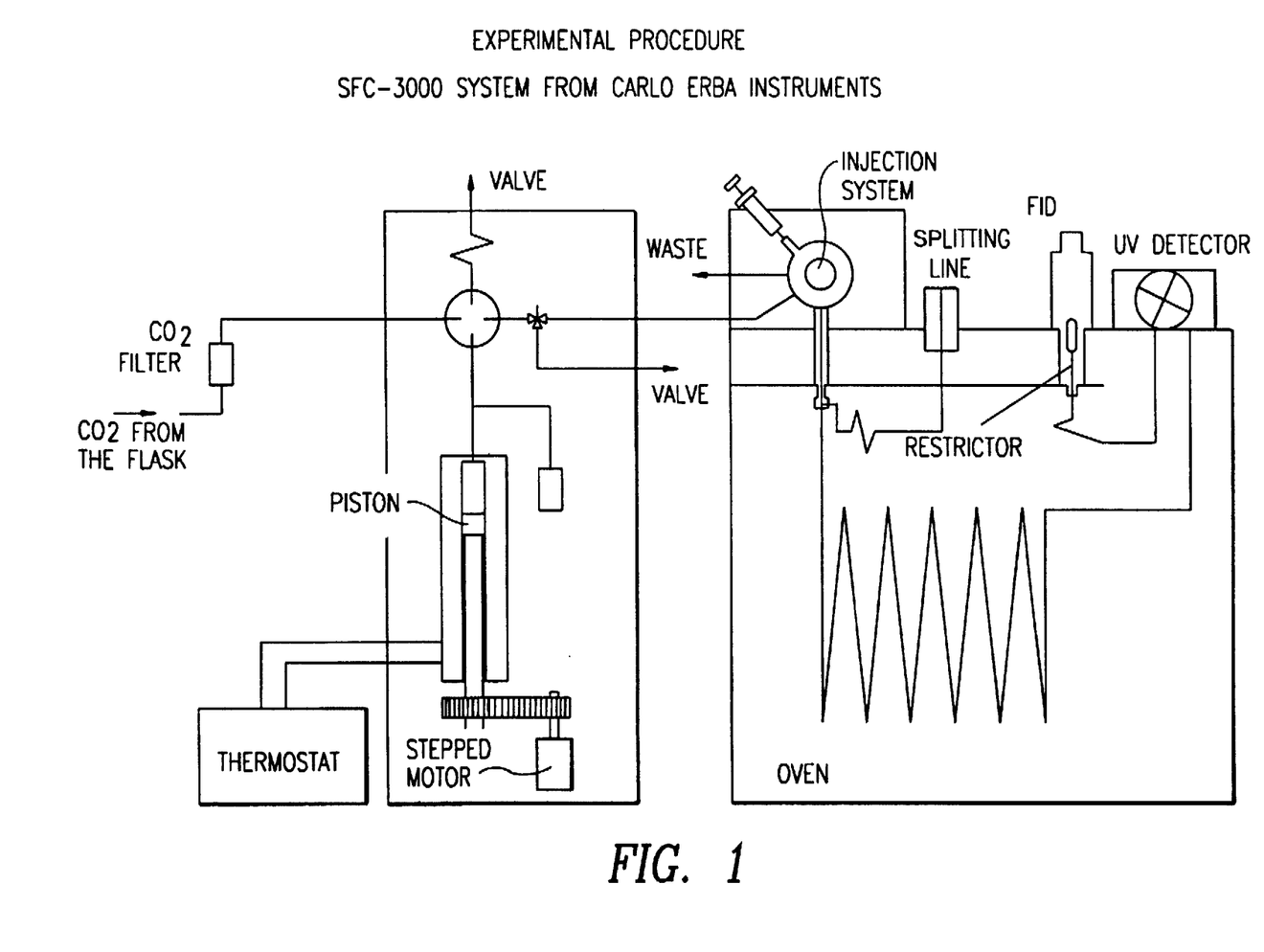
FIG. 1—A schematic view of a SFC-3000 system from Carlo Erba Instruments.
Figure 2:
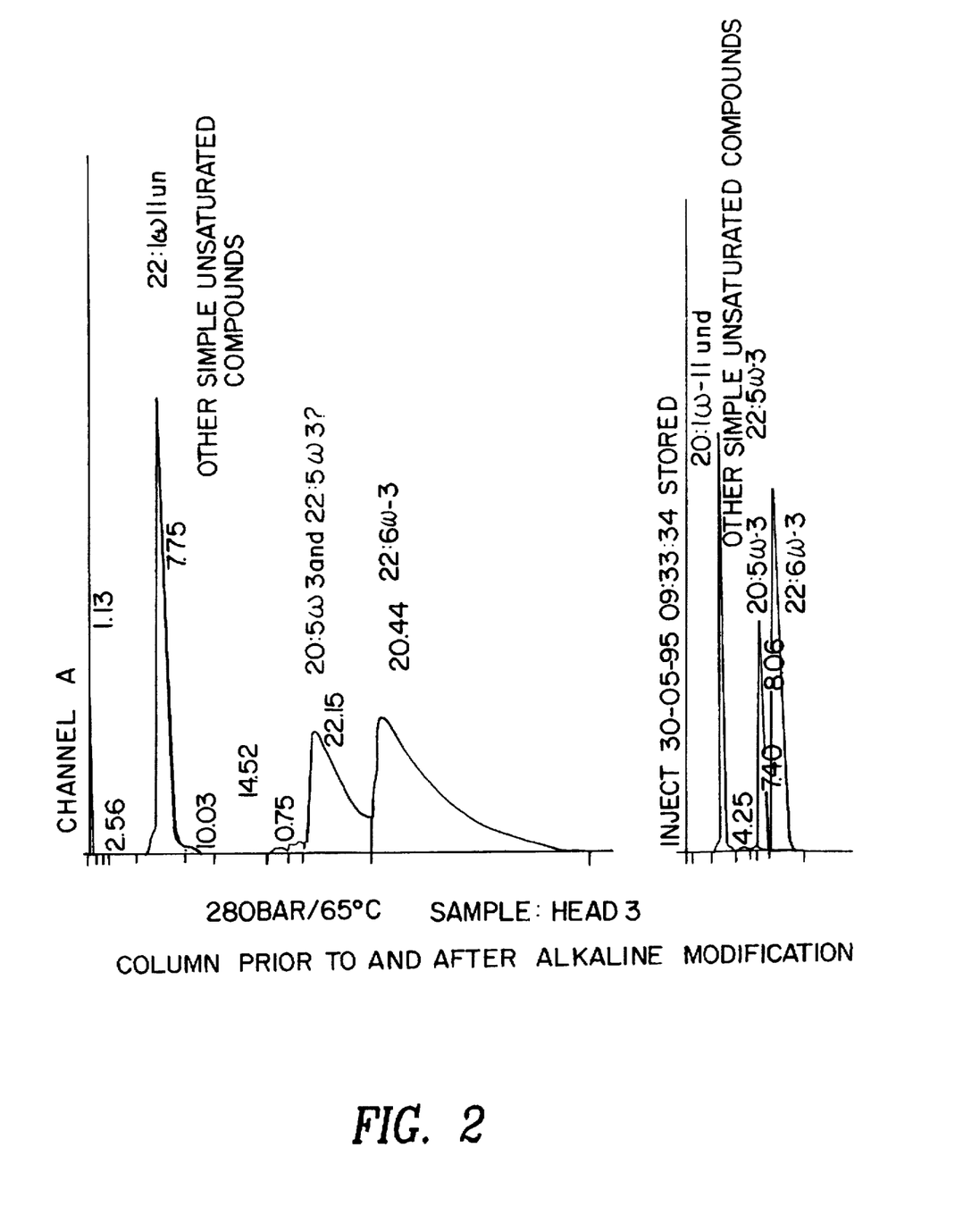
FIG. 2—A chromatogram obtained in Example 1. Stationary phase: aluminum (Spherisorb alumina) Chart velocity: 0.25 cm/min. Attenuation: 64 Concentration: 40 mg/ml n-hexane Detection: FID FIG. 3—A chromatogram obtained in Example 1. Modified column: $Al_2 O_3$ (phase separation). 5 μm Dimension: 250×1 mm Conditions: 240 bar/80° C. Sample: Head 3 Detection: FID (Stationary phase, chart velocity, attentuation and concentration as for FIG. 2)
Figure 3:
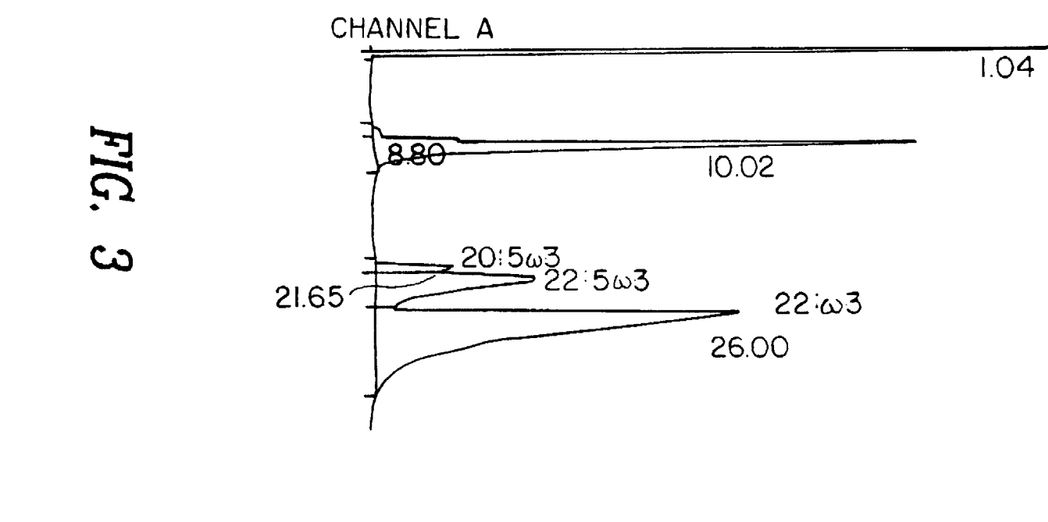

The $CO_2$ is drawn from the cylinder into the pump chamber and is initially condensed to −60° C. therein using a thermostat. The flask is operated via a stepped motor and the mobile phase is thus compressed to the desired pressure. The pressure of the spray pump and well as the temperature of the column oven can be adjusted by computer. The mobile phase flows with the desired pressure through the apparatus and initially passes the injection system. Here, the sample is added via a two-way valve to the mobile phase which is flowing past. The addition time can optionally vary between 0 and 999 msec. The volume of added sample is a constant 0.5 ml. The sample then proceeds with the mobile phase to the column. Here, a separation of the mixture takes place on the basis of different strengths of interaction between the stationary phase and the individual components of the sample solution. The individual components of the mixture are (in the ideal case) eluted in succession from the column. Since the column is situated in an oven, it is also possible to influence the elution behavior via the temperature. The detection (determination) of the substances (inter alia unsaturated fatty acid ethyl esters) separated on the column is effected sequentially via a UV detector and subsequently by means of a flame ionization detector (FID).

EXAMPLE 2

Alkaline Pre-treatment of the Aluminum Oxide Stationary Phase

A chromatography column packed with aluminum oxide is treated with a mixture of 0.1M aqueous sodium hydroxide solution in acetonitrile (90:10% v/v) by rinsing for several hours (12–24 hours).

The pH value of the solution consequently amounts to 13. The column is washed neutral with distilled water, heated to between 50 and 90° C. for about 4–10 hours and subsequently reconditioned with n-heptane for 12–18 hours.

EXAMPLE 3

Performance of the Process (Further Embodiment)

Figure 4:
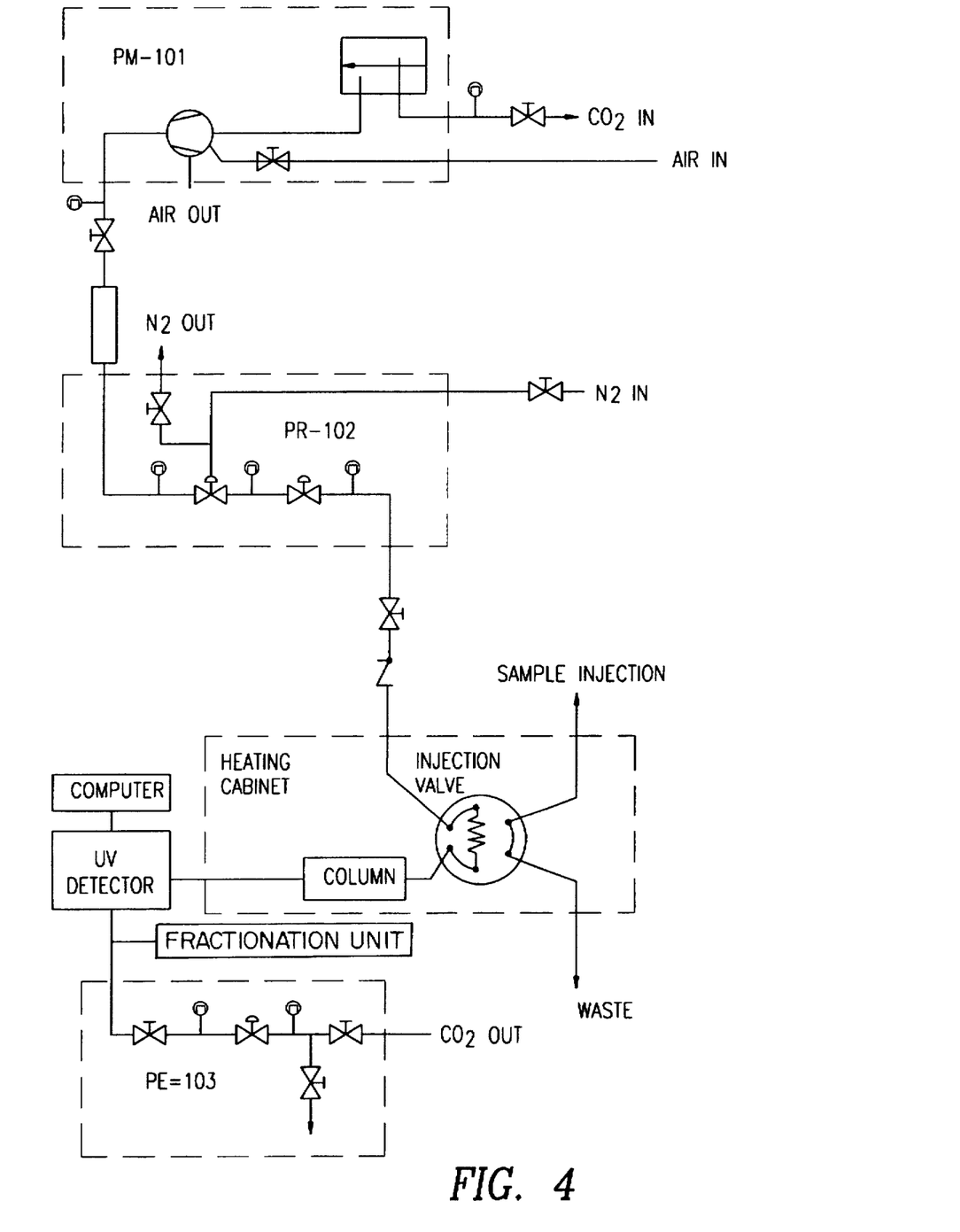
FIG. 4—A schematic view of New Ways of Analytics (NWA) apparatus.
Figure 5:
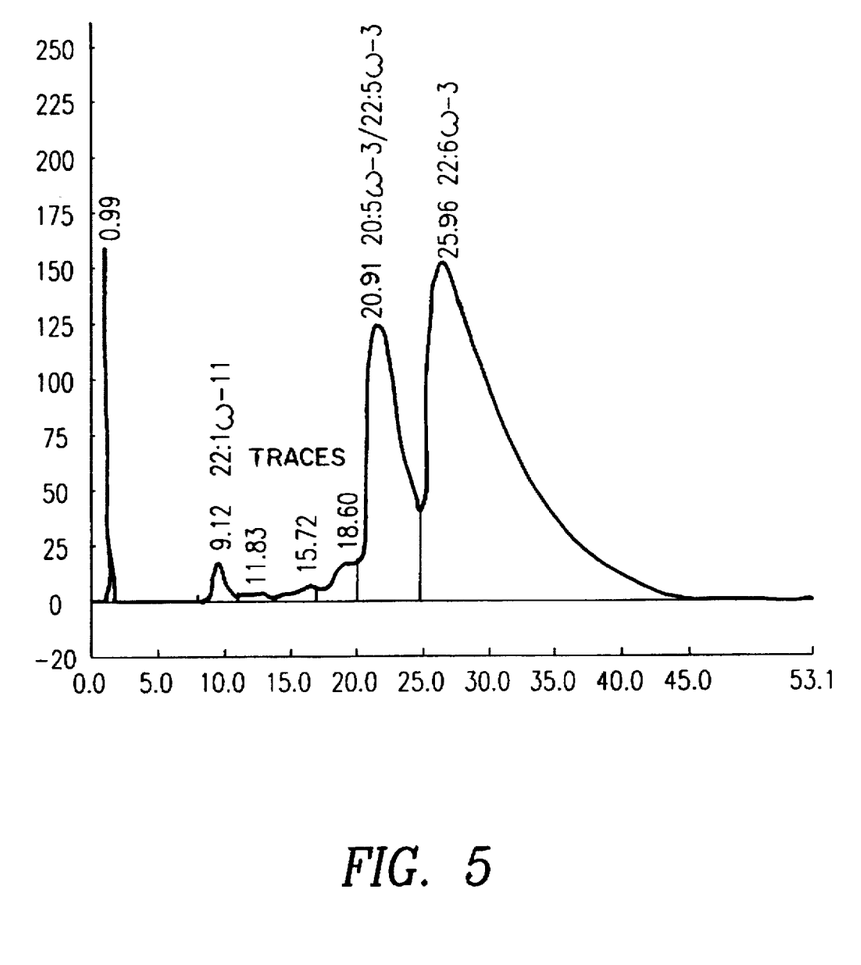
FIG. 5—The resulting UV chromatogram, after employing crushed aluminum oxide as the stationary phase, obtained using the NWA apparatus. Column: ICN 18–32 B mm Dimension: 250×4 mm Conditions: 235 bar/50° C. Injection volume: 5 μl Dilution in hexane 1:1 Detection: UV Sample: Head 3

An apparatus from New Ways of Analytics (see FIG. 4) is used for the operation of columns of large internal diameter and the consequential increase in throughput. The apparatus is continuously supplied with mobile phase via a $CO_2$ conduit. The mobile phase can be operated, depending on the chosen pressure and temperature conditions, in the supercritical (with $CO_2$ above about 31° C. and 73 bar) or also subcritical range. For this purpose, the $CO_2$, which flows from a $CO_2$ container into the thermostat of the pressure module PM-101, is condensed to −6° C. using a thermostat. A pneumatic flask pump condenses the mobile phase to pressures between 300–400 bar. The condensed mobile phase is reduced to the desired pressure in a pressure reduction module PR-102 coupled thereto and additional pressure fluctuations, which result from the operation of the pressure module PM-101, are suppressed. The mobile phase flows at the pressure selected in the pressure reduction module PR-102 through the apparatus and initially passes the injection valve. Here the sample is introduced via a six-way valve (Rheodyne 7125) into the mobile phase which is flowing past. The volume of sample introduced can be varied by selecting appropriate sample sizes of 5 µl up to several milliliters. The sample then proceeds with the mobile phase to the column. A separation of the mixture takes place here on the basis of interactions of different strength between the stationary phase and the individual components of the sample solution. In the ideal case the individual components of the mixture are eluted in succession. Since the column is situated in a heating cabinet, it is also possible to influence the elution behavior via the temperature. The substances separated on the column are recorded via a UV detector and from there are transmitted to chromatography software. The software permits the switching of valves which enables the separated components to be discharged. The pressure release of the supercritical phase is subsequently effected via the pressure release unit PE-103.

The subject invention has been described in terms of its preferred embodiments. Upon reading the specification, various alternative embodiments will become obvious to the skilled artisan. These embodiments are to be considered within the scope and spirit of the subject invention which is only to be limited by the claims that follow and their reasonable equivalents.

What is claimed is:

1. A process for recovering ω-3- and ω-6-polyunsaturated fatty acid entities having at least 16 carbon atoms from a mixture containing the fatty acid entities, which comprises passing the mixture containing the fatty acid entities through a column using an untreated or alkaline pre-treated aluminum oxide stationary phase and a liquid-containing $CO_2$ mobile phase.

2. The process according to claim 1, wherein the aluminum oxide is present as bead-like particles packed as homogeneously as possible, the particle size being about 5 to 25 mm.

3. The process according to claim 1, wherein the aluminum oxide is pre-treated with alkali.

4. The process according to claim 3, wherein the pre-treatment is effected by contacting the aluminum oxide with an aqueous solution of an alkali metal or alkaline earth metal hydroxide in the pH range of from about 10 to about 13 for about 8 to about 20 hours.

5. The process according to claim 4, wherein the solution is supplemented a with water-miscible or water-soluble organic solvent to adjust the viscosity of the aqueous solution.

6. The process according to claim 5, wherein the organic solvent is acetonitrile or acetone.

7. The process according to claim 6, wherein a 10:90 (v/v) mixture of acetonitrile and 0.1M aqueous sodium hydroxide solution is used for the pre-treatment of the aluminum oxide.

8. The process according to claim 1, wherein a fish oil is used as the mixture of fatty acid entities.

9. The process according to claim 8, wherein the fish oil has been previously refined.

10. The process according to claim 8, wherein the fish oil has been previously chemically treated.

11. The process according to claim 10, wherein the fish oil has been previously esterified.

12. The process according to claim 11, wherein the fish oil has been esterified with ethanol.

13. The process according to claim 1, wherein the process is performed in the temperature range of from about 30° C. to about 100° C. and at a pressure of from about 140 bar to about 320 bar.

14. The process according to claim 13, wherein the temperature range is from about 45° C. to about 75° C. and the pressure range is from about 220 bar to about 260 bar.

* * * * *

UNITED STATES PATENT AND TRADEMARK OFFICE
CERTIFICATE OF CORRECTION

PATENT NO. : 5,777,141
DATED : July 7, 1998
INVENTOR(S) : Brunner et al.

It is certified that error appears in the above-identified patent and that said Letters Patent is hereby corrected as shown below:

Column 9, claim 5, line 26, "supplemented a with water-miscible" should be -- supplemented with a water-miscible --

Signed and Sealed this

Tenth Day of November 1998

Attest:

BRUCE LEHMAN

Attesting Officer

Commissioner of Patents and Trademarks